(12) United States Patent
Lee et al.

(10) Patent No.: US 12,377,210 B2
(45) Date of Patent: Aug. 5, 2025

(54) PUMP

(71) Applicant: IPV, Seoul (KR)

(72) Inventors: Do Kyung Lee, Hwaseong-si (KR); Joon Sung Jeon, Yongin-si (KR); Young Wook Chang, Seoul (KR)

(73) Assignee: IPV, Seoul (KR)

( * ) Notice: Subject to any disclaimer, the term of this patent is extended or adjusted under 35 U.S.C. 154(b) by 81 days.

(21) Appl. No.: 18/232,888

(22) Filed: Aug. 11, 2023

(65) Prior Publication Data

US 2023/0381409 A1   Nov. 30, 2023

Related U.S. Application Data

(63) Continuation of application No. PCT/KR2022/002094, filed on Feb. 11, 2022.

(30) Foreign Application Priority Data

Feb. 26, 2021   (KR) .......................... 10-2021-0026314

(51) Int. Cl.
| | |
|---|---|
| *F04B 43/04* | (2006.01) |
| *A61M 5/142* | (2006.01) |
| *A61M 5/145* | (2006.01) |
| *A61M 5/172* | (2006.01) |
| *F04B 53/14* | (2006.01) |
| *A61M 5/158* | (2006.01) |

(52) U.S. Cl.
CPC .... *A61M 5/14586* (2013.01); *A61M 5/14224* (2013.01); *A61M 5/14248* (2013.01); *A61M 5/1723* (2013.01); *F04B 43/04* (2013.01); *F04B 53/143* (2013.01); *A61M 2005/14252* (2013.01); *A61M 2005/1585* (2013.01)

(58) Field of Classification Search
CPC ..... A61M 5/142; A61M 5/145; A61M 5/1452
USPC .................................................... 92/242–245
See application file for complete search history.

(56) References Cited

U.S. PATENT DOCUMENTS

| | | | |
|---|---|---|---|
| 2,741,518 A | * | 4/1956 | Leman ................. F04B 53/144 92/249 |
| 8,152,477 B2 | | 4/2012 | Anex |
| 2008/0029393 A1 | | 2/2008 | Krumme |

FOREIGN PATENT DOCUMENTS

| | | |
|---|---|---|
| JP | H02164373 A | 6/1990 |
| JP | H08238316 A | 9/1996 |
| JP | 2002159574 A | 6/2002 |
| JP | 2006158983 A | 6/2006 |
| JP | 2006-519070 A | 8/2006 |
| JP | 2008500876 A | 1/2008 |
| JP | 2018507027 A | 3/2018 |

(Continued)

OTHER PUBLICATIONS

Kim et al., 'Pump' Mach. Trans. KR 20200021272, Feb. 2020 (Year: 2020).*

*Primary Examiner* — Kenneth J Hansen
(74) *Attorney, Agent, or Firm* — Dinsmore & Shohl LLP; Yongsok Choi, Esq.

(57) ABSTRACT

The present disclosure provides a pump including a housing having a shaft hole, a membrane assembly disposed inside the housing, and a shaft assembly mounted on the housing. The shaft assembly includes a shaft inserted into the shaft hole, and a sealing member disposed on an end portion of the shaft and having a plurality of contact regions on an inner surface of the housing along a longitudinal direction of the shaft.

3 Claims, 15 Drawing Sheets

(56) References Cited

FOREIGN PATENT DOCUMENTS

| | | | |
|---|---|---|---|
| JP | 6594864 B2 | 10/2019 | |
| KR | 10-2016-0068791 A | 6/2016 | |
| KR | 10-2018-0024990 A | 10/2018 | |
| KR | 20200021272 A * | 2/2020 | ............... F04B 9/08 |
| KR | 10-2020-0021272 A | 4/2020 | |
| KR | 1020200038211 A | 4/2020 | |
| KR | 102173812 B1 | 11/2020 | |
| KR | 10-2017-0109593 A | 4/2023 | |

* cited by examiner

PUMP

CROSS-REFERENCE TO RELATED APPLICATIONS

The present application is a continuation of International Application No. PCT/KR2022/002094 filed on Feb. 11, 2022, which claims the benefit of Korean Patent Applications No. 10-2021-0026314 filed on Feb. 26, 2021, in the Korean Intellectual Property Office, the entire disclosure of each of which is incorporated herein by reference.

TECHNICAL FIELD

The present disclosure relates to a pump, and more particularly, to an electro-osmotic pump.

BACKGROUND ART

In general, medical liquid injection devices such as insulin injection devices are used to inject medical liquids into patients' bodies. Although the medical liquid injection devices are sometimes used by professional medical staff such as doctors or nurses, in most cases, the medical liquid injection devices are used by general public such as the patients themselves or guardians.

In the case of diabetic patients, particularly pediatric diabetic patients, it is necessary to inject medical liquids such as insulin into a human body at regular intervals. A patch-type medical liquid injection device that may be used by being attached to a human body for a predetermined period of time has been developed, and such a medical liquid injection device may be used while being attached as a patch type to the human body such as the abdomen or waist of a patient for a predetermined period of time.

In order to increase the effect of the medical liquid injection, the medical liquid injection device needs to be controlled to precisely inject the medical liquid into the body of a patient, and accordingly, it is important to precisely inject a small amount of the medical liquid through a small-sized medical liquid injection device.

Various methods of a driving source for injecting medical liquids are being studied. One of them is to apply a current to a shape memory alloy, but it is complicated to configure and has difficulties in accurately transmitting the driving force.

SUMMARY

Technical Problem

The present disclosure provides a pump that generates a driving force precisely and reliably.

Technical Solution to Problem

One aspect of the present disclosure provides a pump including a housing having a shaft hole, a membrane assembly disposed inside the housing, and a shaft assembly mounted on the housing, wherein the shaft assembly includes a shaft inserted into the shaft hole, and a sealing member disposed on an end portion of the shaft and having a plurality of contact regions on an inner surface of the housing along a longitudinal direction of the shaft.

Advantageous Effects of Disclosure

A pump according to the present disclosure is capable of generating a driving force precisely. A shaft assembly of the pump can receive a force generated by the flow of a fluid and transmit the force to the outside without a loss.

A pump according to the present disclosure can prevent fluid leakage. A sealing member of a shaft assembly has a plurality of contact regions formed due to protrusions, and the plurality of contact regions can completely block the fluid leakage. The sealing member can prevent the fluid leakage due to the flexibility of the protrusions.

A pump according to the present disclosure can be driven with a small driving force. A shaft can linearly reciprocate in an axial direction even when a relatively small driving force is transmitted to a shaft assembly. Protrusions can reduce friction with an inner wall of a housing while maintaining a high degree of sealing, so that the shaft assembly can be easily driven even with a low driving force, and a loss of the driving force can be minimized. Of course, the scope of the present disclosure is not limited by these effects.

DETAILED DESCRIPTION

Figure 1:
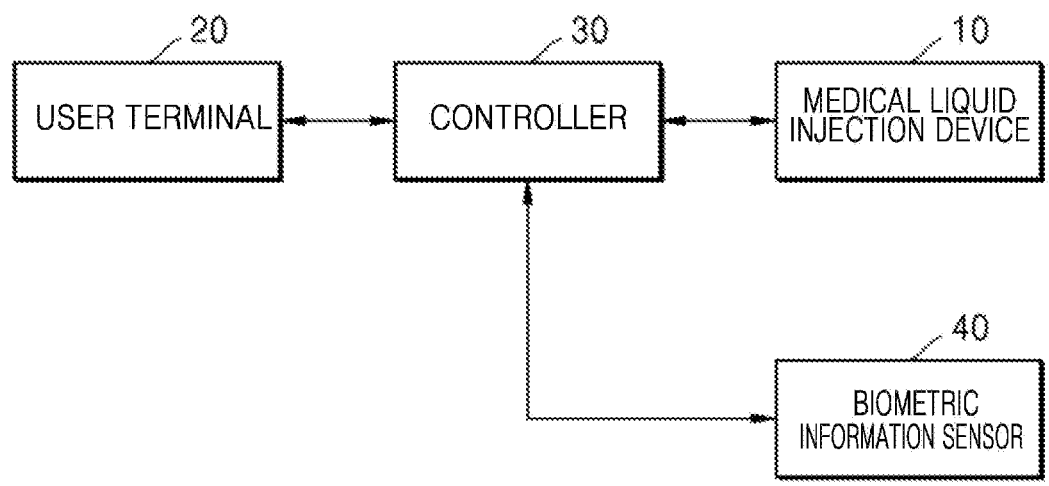
FIG. 1 is a block diagram illustrating a medical liquid injection system according to an embodiment of the present disclosure.

One aspect of the present disclosure provides a pump including a housing having a shaft hole, a membrane assembly disposed inside the housing, and a shaft assembly mounted on the housing, wherein the shaft assembly includes a shaft inserted into the shaft hole, and a sealing member disposed on an end portion of the shaft and having a plurality of contact regions on an inner surface of the housing along a longitudinal direction of the shaft.

In addition, the sealing member may include a body into which the shaft is inserted, a first protrusion protruding from the body in a radial direction of the shaft, and a second protrusion disposed on a side opposite to the first protrusion.

In addition, in the sealing member, at least one of the first protrusion and the second protrusion protrudes from an outer circumferential surface of the body.

In addition, the sealing member may include a body into which the shaft is inserted, a first protrusion protruding from the body in the longitudinal direction of the shaft, and a first groove disposed between the first protrusion and a central axis of the body.

In addition, the shaft may include a first supporter disposed inside the sealing member and extending in a radial direction.

MODE OF DISCLOSURE

While the present disclosure is susceptible to various modifications and alternative forms, specific embodiments thereof are shown by way of example in the drawings and will herein be described in detail. Advantages and features of the present disclosure and a method of achieving the same should become clear with embodiments described below in detail with reference to the drawings. However, the present disclosure is not limited to the embodiments disclosed below, but may be implemented in various forms.

Hereinafter, the embodiments of the present disclosure will be described below in detail with reference to the accompanying drawings, and when the embodiments of the present disclosure are described with reference to the drawings, the same or corresponding components are given the same reference numerals, and repetitive descriptions thereof will be omitted.

In the following embodiments, singular expressions are intended to include plural expressions as well, unless the context clearly indicates otherwise.

In the following embodiments, the terms such as "including," "having," and "comprising" are intended to indicate the existence of features or components disclosed in the specification, and are not intended to preclude the possibility that one or more other features or components may be added.

In cases where certain embodiments may be implemented otherwise, a specific process sequence may be performed differently from the described sequence. For example, two processes described in succession may be performed substantially simultaneously, or may be performed in an order opposite to the order described.

For convenience of description, sizes of components shown in the drawings may be exaggerated or reduced. For example, since the size and thickness of each component shown in the drawings are arbitrarily indicated for convenience of description, the following embodiment is not necessarily limited to what is illustrated.

FIG. 1 is a block diagram illustrating a medical liquid injection system according to an embodiment of the present disclosure.

Referring to FIG. 1, a medical liquid injection system 1 may include a medical liquid injection device 10, a user terminal 20, a controller 30, and a biometric information sensor 40. In the medical liquid injection system 1, a user may drive and control the system by using the user terminal 20, and periodically inject a medical liquid from the medical liquid injection device 10 on the basis of blood sugar information monitored by the biometric information sensor 40.

The medical liquid injection device 10 performs a function of injecting a medical liquid such as insulin, glucagon, anesthetic, pain killer, dopamine, growth hormone, non-smoking aids, or the like to be injected to the user on the basis of data sensed by the biometric information sensor 40.

In addition, the medical liquid injection device 10 may transmit a device state message including information on a remaining battery capacity of the device, whether the device is booted successfully, whether the injection is successful, or the like to the controller 30. Messages transmitted to the controller 30 may be transmitted to the user terminal 20 via the controller 30. Alternatively, the controller 30 may transmit improved data obtained by processing the received messages to the user terminal 20.

In an embodiment, the medical liquid injection device 10 may be provided separately from the biometric information sensor 40 and installed to be spaced apart from an object. In another embodiment, the medical liquid injection device 10 and the biometric information sensor 40 may be provided as one device.

In an embodiment, the medical liquid injection device 10 may be mounted on a user's body. In addition, in another embodiment, the medical liquid injection device may also be mounted on an animal and may inject a medical liquid thereto.

The user terminal 20 may receive an input signal from the user in order to drive and control the medical liquid injection system 1. The user terminal 20 may drive the medical liquid injection device 10 by generating a signal for driving the controller 30, and controlling the controller 30. In addition, the user terminal 20 may display biometric information measured from the biometric information sensor 40, and may display information on a state of the medical liquid injection device 10.

The user terminal 20 refers to a communication terminal that can be used in a wired/wireless communication environment. For example, the user terminal 20 may be a smartphone, a tablet personal computer (PC), a PC, a smart television (TV), a mobile phone, a personal digital assistant (PDA), a laptop computer, a media player, a micro-server, a global positioning system (GPS) device, an electronic book terminal, a digital broadcasting terminal, a navigation device, a kiosk, an MP3 player, a digital camera, a home appliance, a device equipped with a camera, or another mobile or non-mobile computing device. In addition, the user terminal 20 may be a wearable device, such as a watch, glasses, a hairband, or a ring, having a communication function and a data processing function However, a terminal equipped with an application capable of Internet communication as described above may be employed without limitation.

The user terminal 20 may be connected to a pre-registered controller 30 on a one-to-one basis. The user terminal 20 may establish an encryption connection with the controller 30 in order to prevent the controller 30 from being driven and controlled by an external device.

In an embodiment, the user terminal 20 and the controller 30 may be separately provided as separate devices. For example, the controller 30 may be provided to a target person having the medical liquid injection device 10 mounted thereon, and the user terminal 20 may be provided to the target person or a third person. The user terminal 20 may be driven by a guardian so that the safety of the medical liquid injection system 1 may be improved.

In another embodiment, the user terminal 20 and the controller 30 may be provided as one device. The controller 30 and the user terminal 20 provided as one device may communicate with the medical liquid injection device 10 and control injection of a medical liquid.

The controller 30 performs a function of transmitting and receiving data to and from the medical liquid injection device 10, and may transmit a control signal related to injection of a medical liquid such as insulin to the medical liquid injection device 10, and receive a control signal related to a measurement of a biometric value such as a blood sugar level from the biometric information sensor 40.

In an example, the controller 30 may transmit an instruction request for measuring a current state of a user to the medical liquid injection device 10, and receive measurement data, which is generated in response to the instruction request, from the medical liquid injection device 10.

The biometric information sensor 40 may perform a function of measuring a biometric value such as a blood sugar value, blood pressure, or a heart rate of a user according to the purpose. Data measured by the biometric information sensor 40 may be transmitted to the controller 30, and a period and/or injection amount of the medical liquid may be set on the basis of the measured data. The data measured by the biometric information sensor 40 may be transmitted to the user terminal 20 and displayed.

In an example, the biometric information sensor 40 may be a sensor configured to measure a blood sugar level of an object. The biometric information sensor 40 may be a continuous glucose monitor (CGM) sensor. The GSM sensor may be attached to the object and may continuously monitor a blood sugar level.

The user terminal 20, the controller 30, and the medical liquid injection device may perform communication by using a network. For example, the network may include a local area network (LAN), a wide area network (WAN), a value-added network (VAN), a mobile radio communication network, a satellite communication network, or a combination thereof. The network is a data communication network in a comprehensive sense that enables network components to communicate with each other smoothly, and may include a wired Internet, a wireless Internet, or a mobile wireless communication network. In addition, wireless communication may include, for example, wireless LAN (Wi-Fi), Bluetooth, Bluetooth low energy (BLE), Zigbee, Wi-Fi direct (WFD), ultra-wideband (UWB), infrared data association (IrDA), near field communication (NFC), 5th-Generation (5G), or the like, but the present disclosure is not limited thereto.

Figure 2:
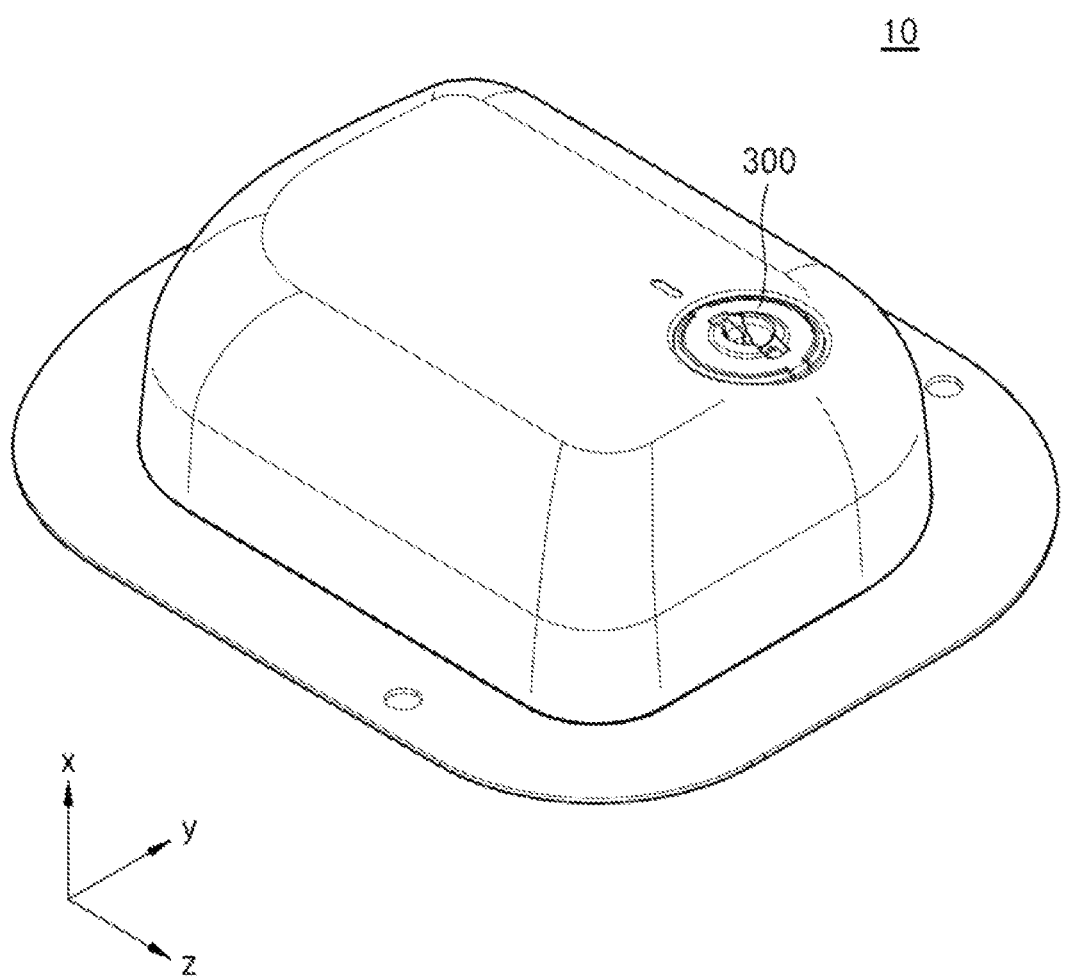
FIG. 2 is a perspective view illustrating the medical liquid injection device according to an embodiment of the present disclosure.

FIG. 2 is a perspective view illustrating the medical liquid injection device according to an embodiment of the present disclosure.

Referring to FIG. 2, the medical liquid injection device 10 may be attached to a user into which a medical liquid is injected, and may inject a medical liquid stored therein to the user in a set amount.

The medical liquid injection device 10 may be used for various purposes depending on the type of medical liquid to be injected. For example, the medical liquid may include an insulin-based medical liquid for a diabetic patient, and may include a medical liquid for other pancreas, a medical liquid for heart, and other various types of medical liquids.

The medical liquid injection device 10 may include a pump 100, a power supply 200, a needle assembly 300, a reservoir unit (not shown), and a plurality of sensor units. When the electro-osmotic pump 100 is driven, a medical liquid stored in the reservoir unit may be discharged to the needle assembly 300 by a generated driving force. Thus, the medical liquid injection device 10 may quantitatively inject the medical liquid to a patient.

Figure 3:
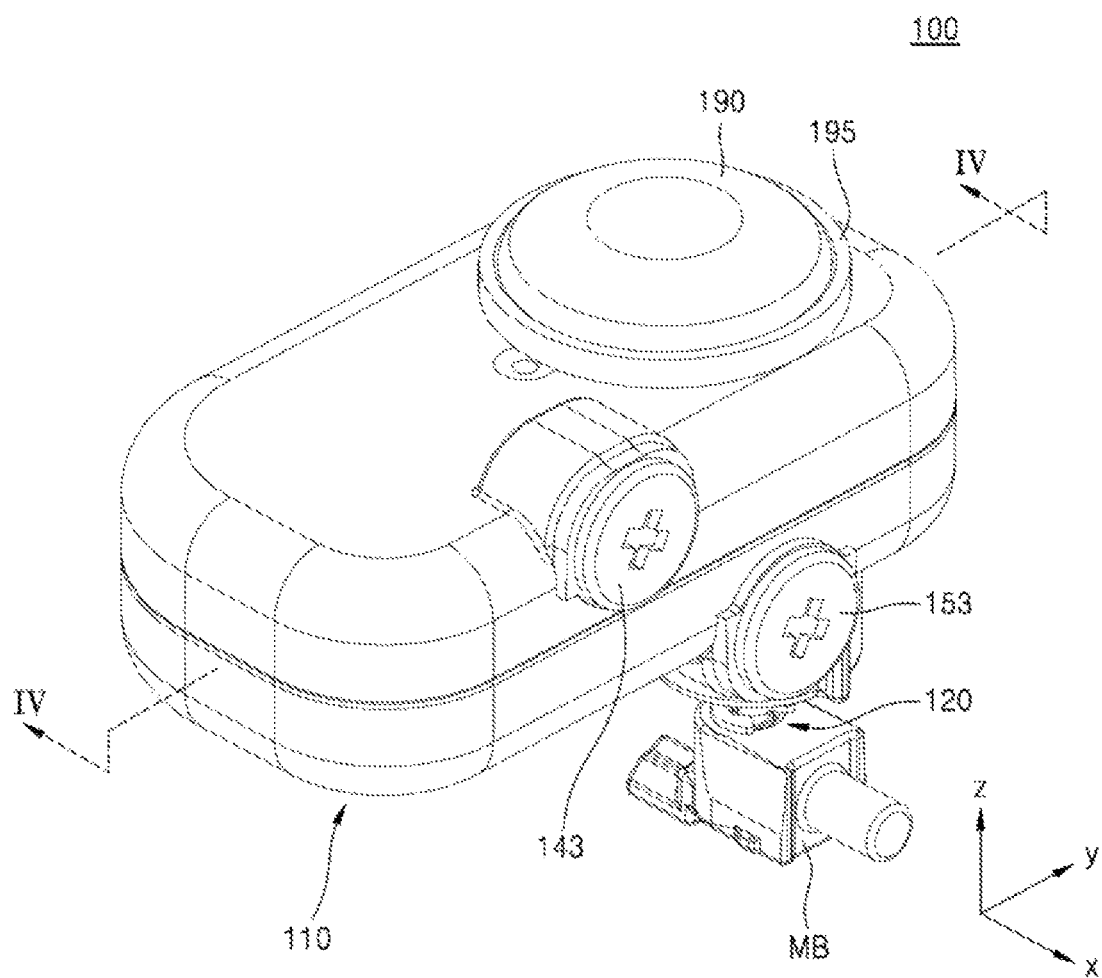
FIG. 3 is a perspective view illustrating an electro-osmotic pump according to an embodiment of the present disclosure.
Figure 4:
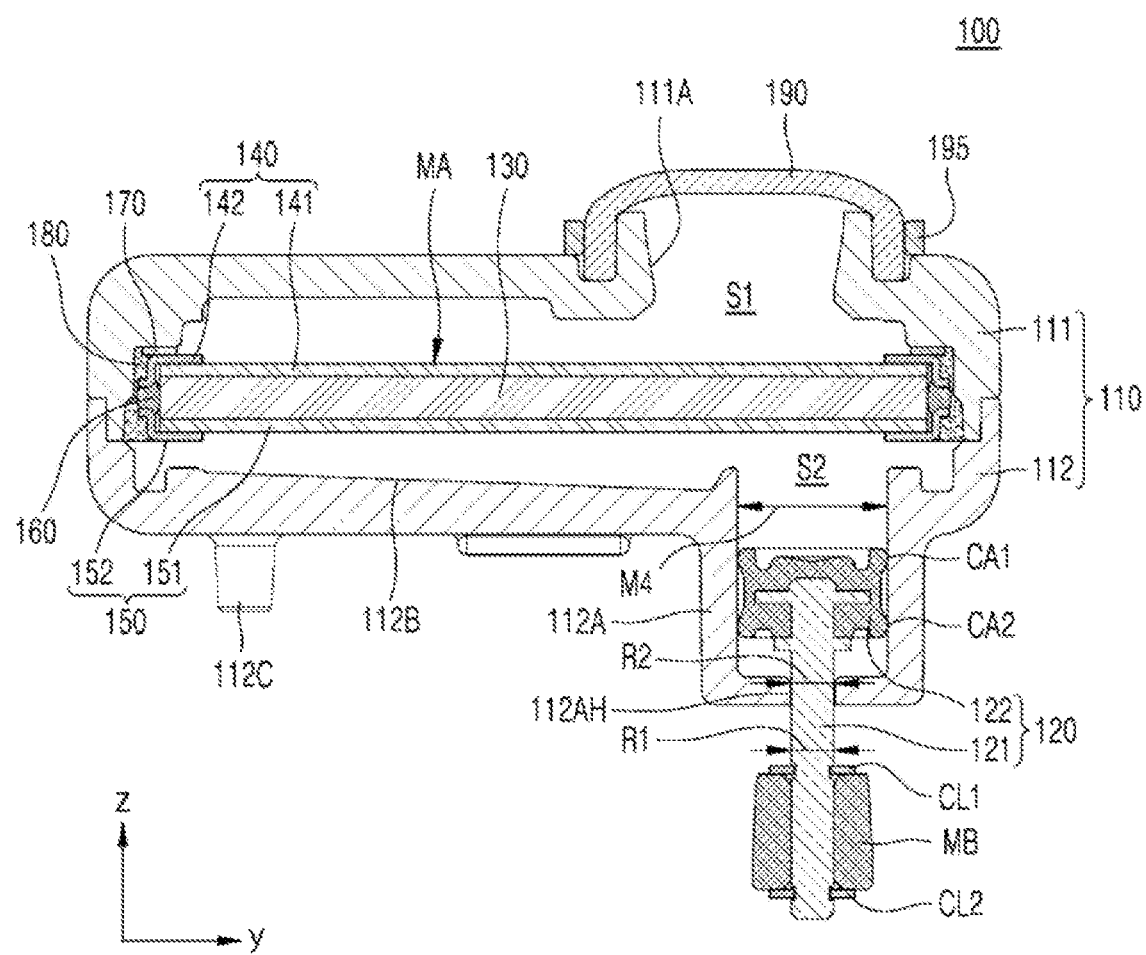
FIG. 4 is a cross-sectional view taken along line IV-IV of FIG. 3.

FIG. 3 is a perspective view illustrating an electro-osmotic pump according to an embodiment of the present disclosure, and FIG. 4 is a cross-sectional view taken along line IV-IV of FIG. 3.

Referring to FIGS. 3 and 4, the pump 100 is a pump for electro-osmotic pumping of a fluid. The pump 100 is not limited to a specific application, and may be installed in various devices or systems to pump fluids. However, hereinafter, for convenience of description, in an embodiment, an electro-osmotic pump applied to a medical liquid injection device will be mainly described.

The electro-osmotic pump 100 may include a housing 110, a shaft assembly 120, a membrane 130, a first electrode body 140, and a second electrode body 150. In addition, the electro-osmotic pump 100 may further include at least one of a first bonding member 160, a second bonding member 170, a third bonding member 180, and a diaphragm member 190.

The housing 110 forms an outer appearance of the electro-osmotic pump 100. The shaft assembly 120 is mounted inside the housing 110, and the shaft assembly 120 may linearly reciprocate along a connection part 112A of the housing 110. The housing 110 includes a shaft hole 112AH, and a shaft 121 may be inserted through the shaft hole 112AH.

In an embodiment, the housing 110 includes a first body 111 and a second body 112, and the first body 111 and the second body 112 may be assembled to form the outer appearance. In another embodiment, the housing may be formed as a single body.

The first body 111 and the second body 112 have an inner space formed when assembled. In the inner space, a membrane assembly MA may be disposed, and a fluid may be stored in the membrane assembly MA.

The first body 111 covers one side of the electro-osmotic pump 100, and may have an opening 111A. The diaphragm member 190 is installed on the opening 111A, and a space in which a fluid is stored or moved may be formed at an inner side of the diaphragm member 190.

The second body 112 covers the other side of the electro-osmotic pump 100, and the shaft assembly 120 may be assembled to the second body 112. The second body 112 includes the connection part 112A, and the shaft assembly 120 may be mounted to the connection part 112A.

The connection part 112A protrudes from the second body 112, and a sealing member 122 of the shaft assembly 120 may be installed in the connection part 112A. The connection part 112A includes the shaft hole 112AH, and the shaft 121 having a predetermined length may extend to the outside of the housing 110 through the shaft hole 112AH.

In an embodiment, the shaft hole 112AH may be formed in the connection part 112A extending from one side of the second body 112 of the housing 110, and a diameter R2 of the shaft hole 112AH may be formed to be substantially equal to a diameter R1 of the shaft 121.

In an embodiment, the connection part 112A has a predetermined inner diameter M4 therein, and the inner diameter M4 of the connection part 112A may be set to be smaller than a first outer diameter M1 of the sealing member 122. Thus, the sealing member 122 is in close contact with an inner circumferential surface of the connection part 112A, thereby preventing a fluid from leaking out.

The second body 112 may include an inclined surface 112B having an inclination and disposed on an inner circumferential surface thereof. The inclined surface 112B may have the inclination that decreases in height from an edge of the second body 112 toward the connection part 112A. Since the inclined surface 112B has the inclination descending toward the connection part 112A, when the electro-osmotic pump 100 is driven, a fluid is guided to an inner space of the connection part 112A, and in particular, the fluid is guided to move to the connection part 112A. Since the fluid moving toward the connection part 112A transmits a driving force generated by the electro-osmotic pump 100 to the shaft assembly 120, the inclined surface 112B may effectively transmit the driving force to the shaft assembly 120.

The second body 112 may include an inlet 112C at one side thereof. A fluid may be injected into the housing 110 through the inlet 112C.

Figure 5:
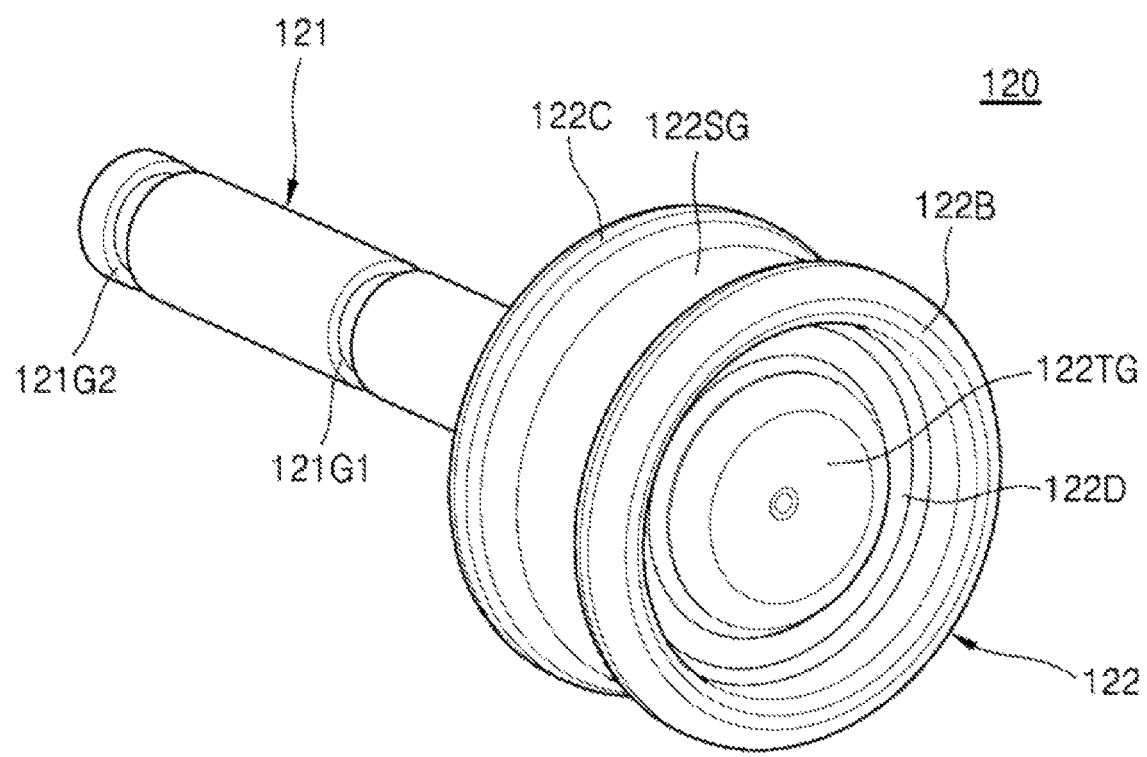
FIGS. 5 and 6 are perspective views illustrating a shaft assembly of FIG. 4.
Figure 6:
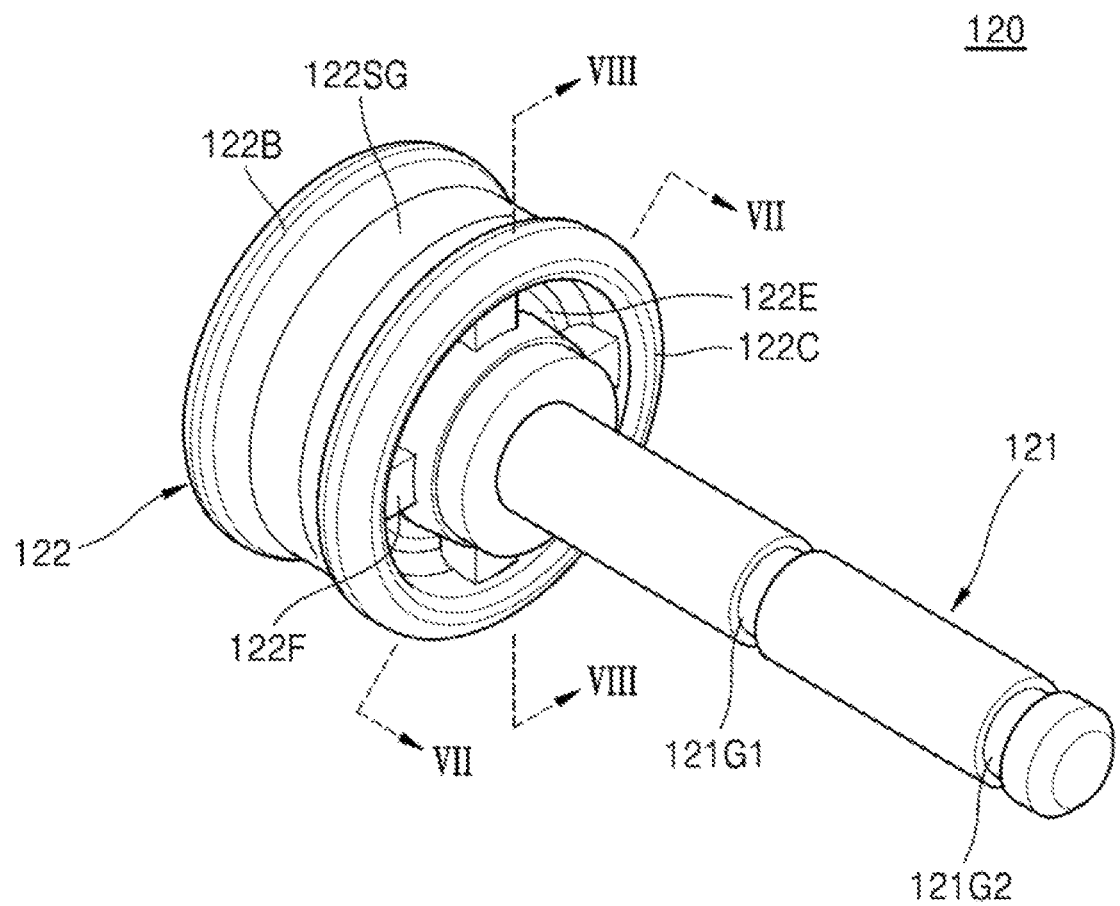
Figure 7:
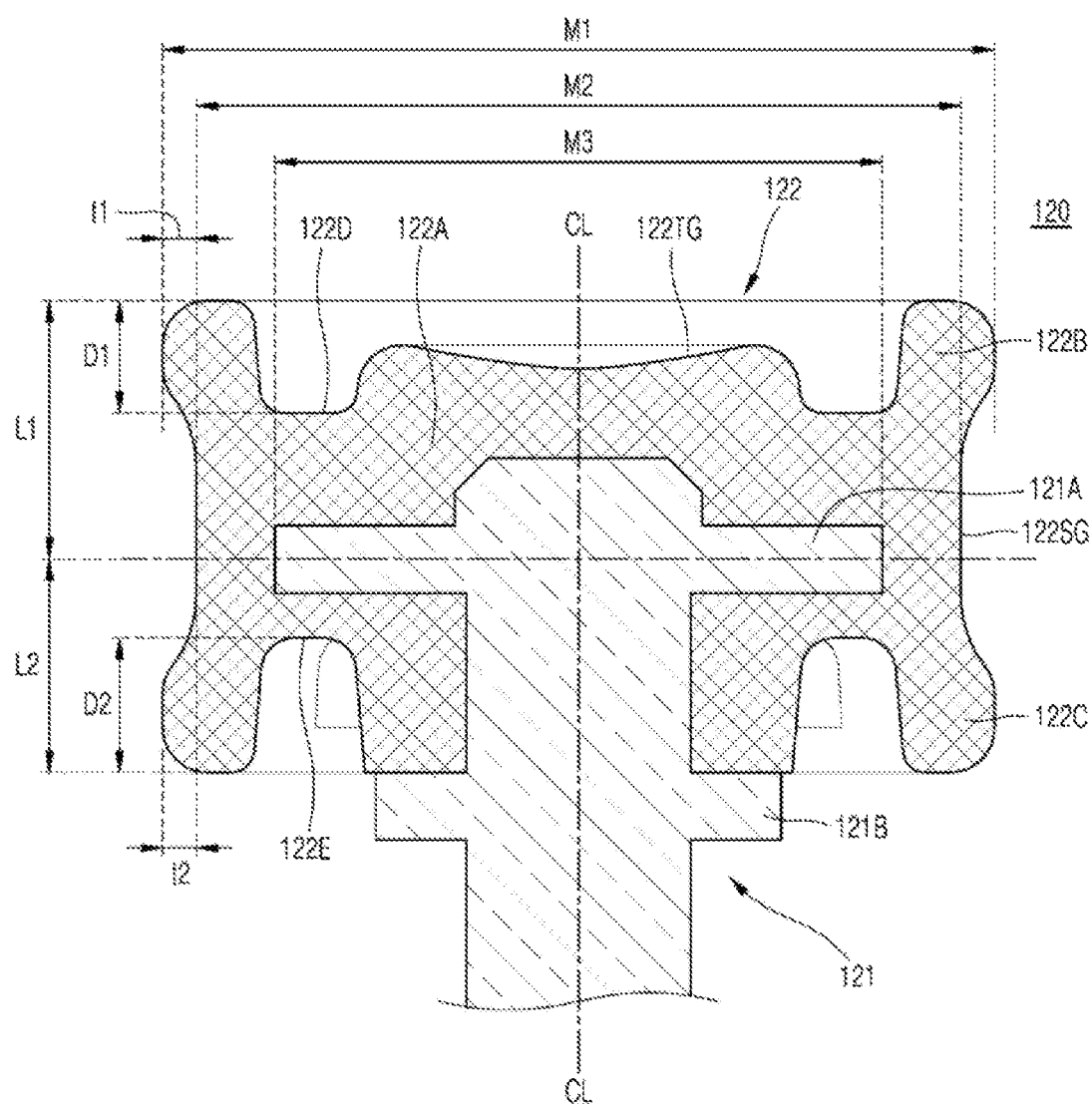
FIG. 7 is a view illustrating a portion of a cross-sectional view taken along line VI-VI of FIG. 6.
Figure 8:
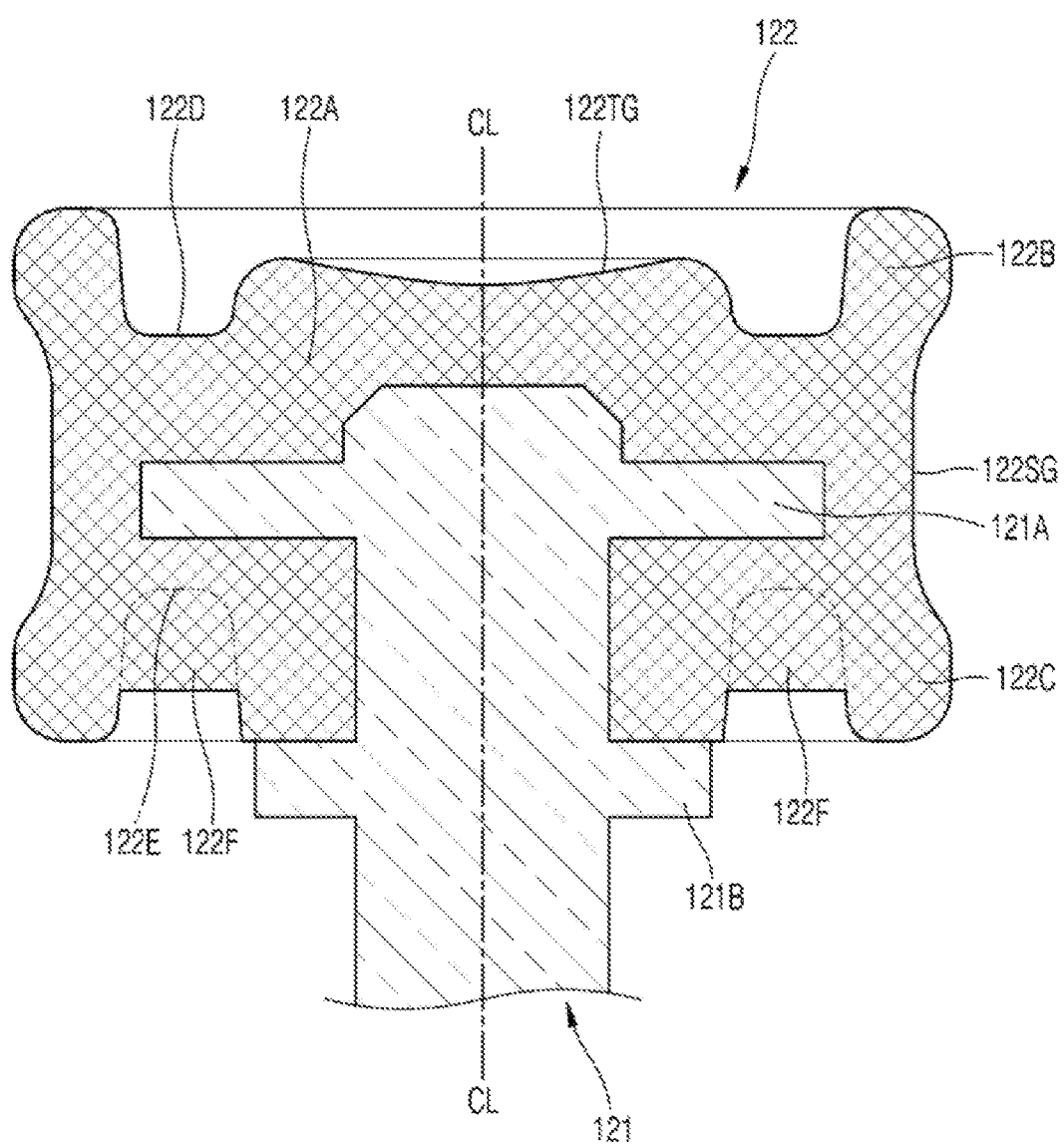
FIG. 8 is a view illustrating a portion of a cross-sectional view taken along line VII-VII of FIG. 6.
Figure 9:
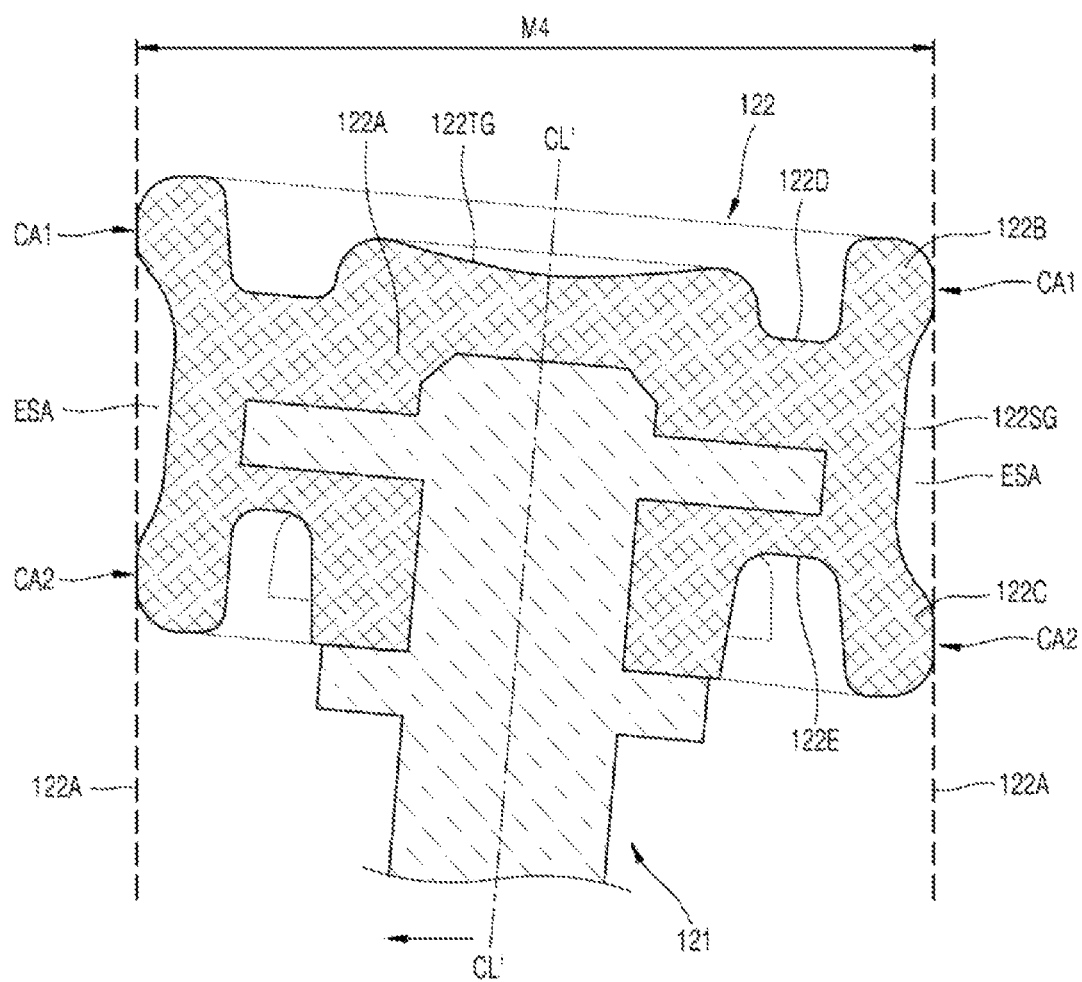
FIG. 9 is a view illustrating the shaft assembly of FIG. 7 in one driving state.

FIGS. 5 and 6 are perspective views illustrating the shaft assembly of FIG. 4, FIG. 7 is a view illustrating a portion of a cross-sectional view taken along line VI-VI of FIG. 6, FIG. 8 is a view illustrating a portion of a cross-sectional view taken along line VII-VII of FIG. 6, and FIG. 9 is a view illustrating the shaft assembly of FIG. 7 in one driving state.

Referring to FIGS. 4 to 9, the shaft assembly 120 may be mounted in the connection part 112A of the housing 110 and may include the shaft 121 and the sealing member 122.

The shaft 121 may be inserted into the shaft hole 112AH. The shaft 121 may have a portion disposed inside the housing 110 and another portion extending through the shaft hole 112AH to the outside of the housing 110. The shaft 121 may linearly reciprocate in a Z-axis direction in FIG. 4.

The shaft 121 may have a supporter by which the sealing member 122 is supported. One or more supporters may be provided so that the shaft 121 and the sealing member 122 may be firmly assembled.

A first supporter 121A may be disposed inside the sealing member 122. The first supporter 121A may extend a predetermined length from a body of the shaft 121 in a radial direction. The first supporter 121A may have a greater rigidity than the sealing member 122, allowing the shaft assembly 120 to transmit a driving force while preventing fluid leakage.

A second supporter 121B may be disposed to support an outer side of the sealing member 122. For example, the second supporter 121B may support a body 122A of the sealing member 122.

A moving member MB may be installed at an end portion of the shaft 121. The moving member MB is connected to another external device, and a driving force may be transmitted to the outside by a linear reciprocating motion of the moving member MB.

The shaft 121 may have a first fixing groove 121G1 and a second fixing groove 121G2. A first clip CL1 may be mounted in the first fixing groove 121G1, and a second clip CL2 may be mounted in the second fixing groove 121G2, so that the moving member MB may be fixed to the shaft 121.

The sealing member 122 is disposed at an end portion of the shaft 121, and may have a plurality of contact regions on an inner surface of the housing 110 along a longitudinal direction of the shaft 121.

The sealing member 122 may include the body 122A into which the shaft 121 is inserted and a plurality of protrusions.

In an example, the sealing member 122 may include a first protrusion 122B protruding from the body 122A in the radial direction of the shaft 121 and a second protrusion 122C disposed on a side opposite to the first protrusion 122B. At least one of the first protrusion 122B and the second protrusion 122C may protrude from an outer circumferential surface of the body 122A.

In an example, the sealing member 122 may have the first protrusion 122B protruding from the body 122A in the longitudinal direction of the shaft 121 and a first groove 122D disposed adjacent to the first protrusion 122B. The first protrusion 122B may protrude in the longitudinal direction due to the first groove 122D.

The first supporter 121A of the shaft 121 may be mounted in the body 122A. The first supporter 121A extends to a predetermined length in the radial direction, so that the sealing member 122 is firmly mounted on the shaft 121. Accordingly, when a force generated by the movement of a fluid is transmitted to the sealing member 122, the force may be transmitted to the shaft 121 without a loss.

The sealing member 122 may include the plurality of protrusions. Each of the protrusions forms a contact region with an inner circumferential surface of the housing 110, and the contact regions may prevent fluid leakage. The sealing member 122 has the plurality of contact regions to prevent a fluid from leaking.

The sealing member 122 may be formed of a flexible material. The sealing member 122 may be deformed in shape so as to be in close contact with the inner circumferential surface of the connection part 112A, and may be formed of a material having a predetermined elastic force. For example, the sealing member 122 may be made of a material such as rubber, silicone, synthetic resin, or a combination thereof.

The first protrusion 122B may protrude from the body 122A in the radial direction of the shaft 121. The first protrusion 122B may protrude from a front end portion of the body 122A.

The first protrusion 122B may be in contact with the inner circumferential surface of the connection part 112A to form a first contact region CA1. The first outer diameter M1 of the first protrusion 122B may be formed to be greater than the inner diameter M4 of the connection part 112A, so that the first protrusion 122B is in close contact with the connection part 112A to prevent fluid leakage.

In an embodiment, the first protrusion 122B may extend along a perimeter of the body 122A and have a ring shape. However, the first protrusion is not limited thereto, and may be disposed only on a partial perimeter of the body.

The second protrusion 122C may protrude from the body 122A in the radial direction of the shaft 121. The second protrusion 122C may protrude from a rear end portion of the body 122A, which is an opposite side of the first protrusion 122B.

The second protrusion 122C may be in contact with the inner circumferential surface of the connection part 112A to form a second contact region CA2. The first outer diameter M1 of the second protrusion 122C may be formed to be greater than the inner diameter M4 of the connection part 112A, so that the second protrusion 122C is in close contact with the connection part 112A to prevent fluid leakage.

In an embodiment, the second protrusion 122C may extend along a perimeter of the body 122A and have a ring shape. However, the second protrusion is not limited thereto, and may be disposed only on a partial perimeter of the body. The driving force may be transmitted to the shaft assembly 120 without a loss.

The first protrusion 122B and the second protrusion 122C are disposed to face each other in the sealing member 122, and a sidewall 122SG whose surface is concave may be formed between the first protrusion 122B and the second protrusion 122C.

The sidewall 122SG may have a predetermined second outer diameter M2. The second outer diameter M2 of the sidewall 122SG may be set to be greater than a third outer diameter M3 of the first supporter 121A and smaller than the first outer diameter M1 of the first protrusion 122B.

The first protrusion 122B may have a protrusion height of t1 from a low point of the sidewall 122SG, and the second protrusion 122C may have a protrusion height of t2 from the low point of the sidewall 122SG. Since the first protrusion 122B and the second protrusion 122C protrude from the sidewall 122SG in the radial direction, when the sealing member 122 is mounted on the inner circumferential surface of the connection part 112A, an allowable space ESA may be formed between the sidewall 122SG and the inner circumferential surface of the connection part 112A, which allows changes in shapes of the first protrusion 122B and the second protrusion 122C, so that the first protrusion 122B and the second protrusion 122C may be in strongly close contact with the inner circumferential surface of the connection part 112A.

The first groove 122D may be disposed on an inner side of the first protrusion 122B. A depth of D1 may be formed between a bottom of the first groove 122D and a terminating end of the first protrusion 122B. The first groove 122D may be disposed between the first protrusion 122B and the body 122A to increase a close-contact force of the first protrusion 122B.

A second groove 122E may be disposed on an inner side of the second protrusion 122C. A depth of D2 may be formed between a bottom of the second groove 122E and a terminating end of the second protrusion 122C. The second groove 122E may be disposed between the second protrusion 122C and the body 122A to increase a close-contact force of the second protrusion 122C.

The first groove 122D allows the first protrusion 122B to be deformed in the radial direction, and the second groove 122E allows the second protrusion 122C to be deformed in the radial direction. For example, even when the shaft 121 is moving, the first protrusion 122B and the second protrusion 122C are deformed in shape and thus may maintain the first contact region CA1 and the second contact region CA2.

In an embodiment, the depth of D1 of the first groove 122D and the depth of D2 of the second groove 122E may be set to be different from each other. In an example, D2 may be formed to be longer than D1.

Since the first groove 122D is in contact with the fluid stored in the housing 110, the first contact region CA1 should maintain a higher level of sealing than the second contact region CA2. Even when the shaft 121 is moving, the first protrusion 122B should be strongly supported on the inner sidewall 122SG while allowing a slight deformation to minimize the movement of the shaft assembly 120. The second protrusion 122C should be relatively more flexible compared to the first protrusion 122B to prevent a liquid from leaking out of the housing 110. Accordingly, by setting the depth D1 of the first groove 122D be smaller than the depth D2 of the second groove 122E, the first protrusion 122B maintains the sealing while minimizing the movement of the shaft 121, and the second protrusion 122C has higher flexibility than the first protrusion 122B to prevent fluid leakage.

In an embodiment, the first protrusion 122B and the second protrusion 122C may be asymmetrically disposed on the first supporter 121A. In an example, a first distance L1 from the center of the first supporter 121A to an end of the first protrusion 122B may be formed to be greater than a second distance L2 from the center of the first supporter 121A to an end of the second protrusion 122C.

The first protrusion 122B is in contact with the fluid stored in the electro-osmotic pump 100, and the front of the sealing member 122 should effectively transmit a force generated according to the movement of the fluid to the shaft 121. Since the first distance L1 is formed to be greater than the second distance L2, the sealing member 122 has a larger volume at the front of the first supporter 121A than at the rear of the first supporter 121A. In particular, since the depth D1 of the first groove 122D is set to be smaller than the depth D2 of the second groove 122E, the sealing member 122 has a larger volume at the front of the first supporter 121A than at the rear of the first supporter 121A. Thus, the sealing member 122 maintains a significant volume at the front, so that the force generated according to the movement of the fluid may be effectively transmitted to the shaft 121.

The sealing member 122 has the first outer diameter M1 of the first protrusion 122B or the second protrusion 122C and the second outer diameter M2 of the sidewall 122SG. The first outer diameter M1 is set to be greater than the inner diameter M4 of the connection part 112A, so that the fluid does not leak when the shaft assembly 120 is driven. The second outer diameter M2 is set to be smaller than the inner diameter M4 of the connection part 112A to increase the flexibility of the sealing member 122.

The third outer diameter M3 of the first supporter 121A may be set to be smaller than the first outer diameter M1 of the sealing member 122 and smaller than the second outer diameter M2. The first supporter 121A is disposed inside the sealing member 122, and may reinforce the rigidity of the sealing member 122.

The first supporter 121A extends from the shaft 121, and may extend to at least partially overlap the first groove 122D or the second groove 122E. The first supporter 121A extends to the first groove 122D or the second groove 122E, so that a relatively thin portion of the sealing member 122 may be reinforced in a height direction. In addition, since the first supporter 121A extends to the first groove 122D or the second groove 122E, a section between a terminating end of the first supporter 121A and the sidewall 122SG, which is a relatively thin section, may be reinforced in a radial direction.

Referring to FIG. 8, the sealing member 122 may further include a reinforcing block 122F. The reinforcing block 122F may be disposed in the second groove 122E. One or more reinforcing blocks 122F are disposed along the second groove 122E to reinforce rearward rigidity of the sealing member 122.

A plurality of reinforcing blocks 122F may be disposed to be spaced apart from each other along the second groove 122E. The reinforcing block 122F supports an inner side of the second protrusion 122C to prevent the second protrusion 122C from being excessively deformed.

In an optional embodiment, the sealing member 122 may have a concave surface 122TG. The sealing member 122 is disposed forward in a direction of an axis CL. Since a fluid is guided to the concave surface 122TG of the sealing member 122, the driving force of the electro-osmotic pump 100 may be transmitted in the direction of the axis CL of the shaft assembly 120.

Referring to FIG. 9, even when a driving axis CL' of the shaft assembly 120 is slightly misaligned, the sealing member 122 of the shaft assembly 120 may maintain the contact regions, so that fluid leakage may be prevented.

The first protrusion 122B forms the first contact region CA1, and the second protrusion 122C forms the second contact region CA2. The plurality of contact regions are formed in the direction of the axis CL to prevent the fluid from leaking between the sealing member 122 and the inner circumferential surface of the housing 110.

When the sealing member 122 is mounted in the connection part 112A, the allowable space ESA is formed between the first contact region CA1 and the second contact region CA2. The allowable space ESA is defined by the inner circumferential surface of the connection part 112A, the sidewall 122SG of the sealing member 122, the first protrusion 122B, and the second protrusion 122C, and the allowable space ESA may allow the first protrusion 122B and the second protrusion 122C to be deformed in shape.

Since the plurality of protrusions of the sealing member 122 come into contact with the inner circumferential surface of the housing 110 to form the contact regions, the shaft assembly 120 may prevent the fluid from leaking to the outside of the housing 110. In particular, since the first protrusion 122B and the second protrusion 122C are slightly deformed in shape and come into close contact with the inner circumferential surface of the housing 110, fluid leakage may be prevented.

The shaft assembly 120 may easily perform a linear reciprocating motion by the movement of the fluid, while maintaining a high sealing force by the protrusions. Even though the protrusions of the sealing member 122 come into highly close contact with the inner circumferential surface of the housing 110, since the protrusions have flexibility, the protrusions can move along the inner circumferential surface of the housing 110, particularly the inner circumferential surface of the connection part 112A, even with a relatively weak force. Thus, the shaft assembly 120 may linearly reciprocate even when the driving force generated by the movement of the fluid passing through the membrane assembly MA is low.

In addition, since the protrusions of the sealing member 122 have flexibility, the shaft assembly 120 may be easily driven when the electro-osmotic pump 100 is initially driven. When the electro-osmotic pump 100 is stored in an undriven state for a long time, the sealing member 122 may stick to the inner circumferential surface of the housing 110. In this case, the shaft assembly 120 can start driving only when a strong driving force is generated. In the sealing member 122 of the shaft assembly 120 according to the present disclosure, the sealing member 122 can easily perform a linear reciprocating motion during initial driving since the protrusions have high flexibility.

Figure 10:
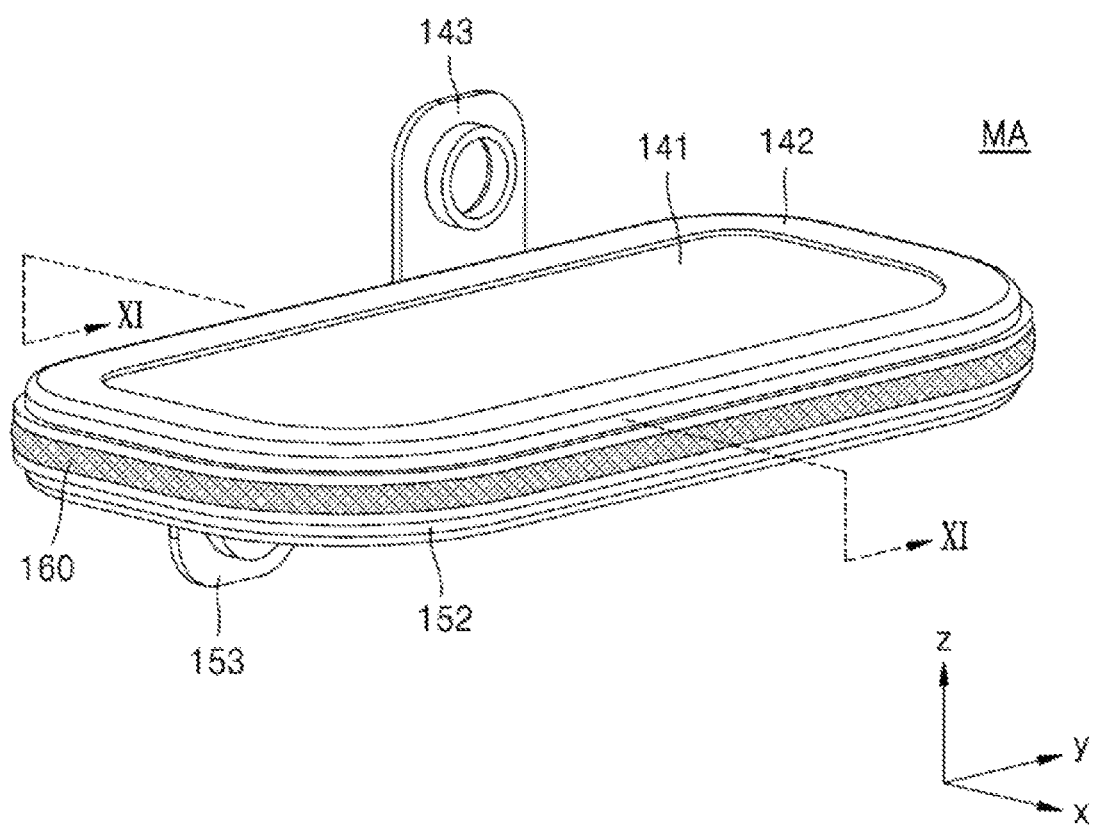
FIG. 10 is a perspective view illustrating a membrane assembly of FIG. 4.
Figure 11:
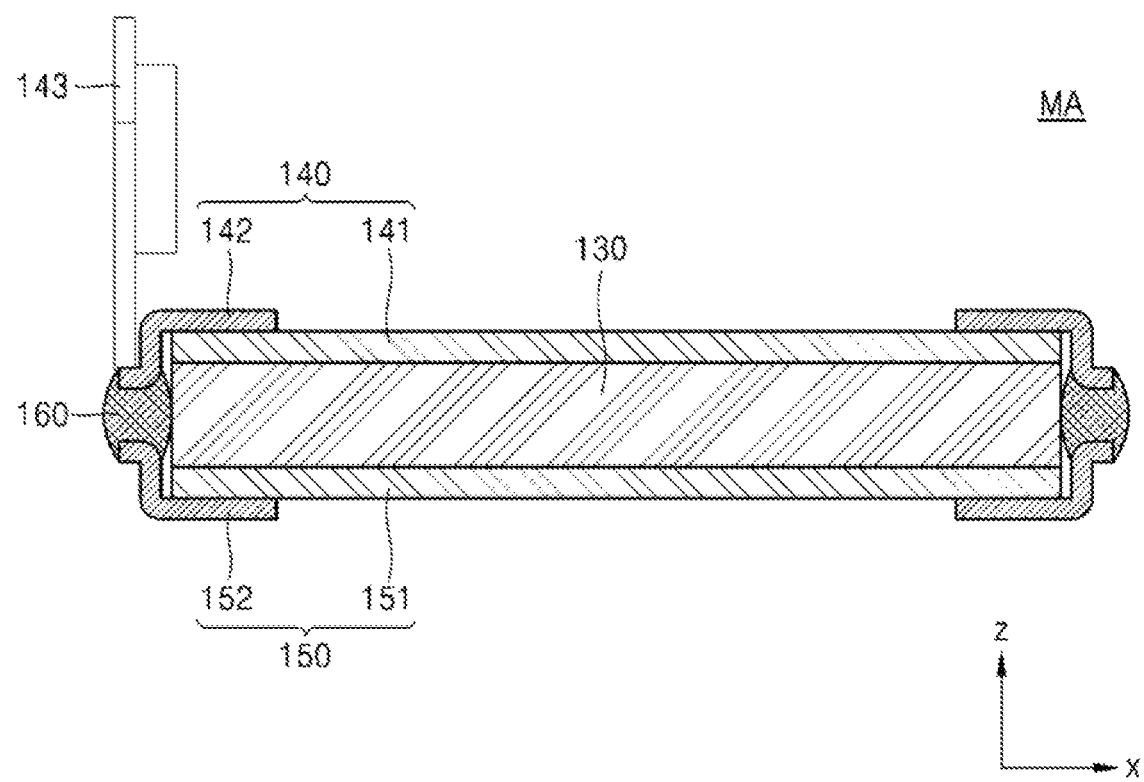
FIG. 11 is a cross-sectional view taken along line XI-XI of FIG. 10.

FIG. 10 is a perspective view illustrating the membrane assembly of FIG. 4, and FIG. 11 is a cross-sectional view taken along line XI-XI of FIG. 10.

Referring to FIGS. 10 and 11, the membrane assembly MA is mounted in the housing 110, and may generate a driving force for the electro-osmotic pump 100.

The membrane 130 may be disposed in an inner space of the housing 110. The inner space includes a first space S1 and a second space S2 respectively located on opposite sides of the membrane 130.

In FIG. 4, a space farther from the shaft assembly 120 based on the membrane 130 is represented as the first space S1 and a space closer to the shaft assembly 120 based on the membrane 130 is represented as the second space S2.

The membrane 130 may have a porous structure through which the fluid and ions may pass. The membrane 130 may be, for example, a frit-type membrane that is fabricated by sintering spherical silica with heat. For example, the spherical silica used to form the membrane may have a diameter of about 20 nm to about 500 nm, in particular, a diameter of about 30 nm to about 300 nm, and in more particular, a diameter of about 40 nm to about 200 nm.

When the diameter of the spherical silica satisfies the above range, a pressure caused by a first fluid passing through the membrane 130, that is, a sufficient pressure to move the shaft assembly 120, may be generated.

In the above-described embodiment, the membrane 130 includes the spherical silica, but the membrane 130 is not limited thereto.

In another embodiment, a kind of a material included in the membrane 130 is not particularly limited as long as the material is a material that may cause an electrokinetic phenomenon due to zeta potential, for example, porous silica or porous alumina.

The membrane 130 may have a thickness of about 20 μm to about 10 mm, in particular, about 300 μm to about 5 mm, and in more particular, about 1000 μm to about 4 mm.

The first electrode body 140 and the second electrode body 150 are respectively disposed on opposite sides of the membrane 130. The first electrode body 140 may include a first porous plate 141 and a first strip 142 disposed on a first side of the membrane 130. The second electrode body 150 may include a second porous plate 151 and a second strip 152 disposed on a second side of the membrane 130.

The first porous plate 141 and the second porous plate 151 may be arranged to be respectively in contact with opposite main surfaces of the membrane 130. The first porous plate 141 and the second porous plate 151 may effectively move the fluid and the ions through the porous structure.

The first porous plate 141 and the second porous plate 151 may each have a structure in which an electrochemical reaction material is formed on a porous base layer. The electrochemical reaction material may be formed by being electrodeposited or coated on the porous base layer by a method such as electroless plating, vacuum deposition, coating, sol-gel process, or the like.

The porous base layer may be an insulator. For example, the porous base layer may include one or more selected from non-conductive ceramic, a non-conductive polymer resin, non-conductive glass material, and a combination thereof.

The non-conductive ceramic may include, for example, one or more selected from the group consisting of rock wool, gypsum, ceramics, cement, and a combination thereof, and in particular, one or more selected from the group consisting of rock wool, gypsum, and a combination thereof, but the present disclosure is not limited thereto.

The non-conductive polymer resin may include one or more selected from the group consisting of: for example, synthetic fiber selected from the group consisting of polypropylene, polyethylene terephthalate, polyacrylonitrile, and a combination thereof; natural fiber selected from the group consisting of wool, cotton, and a combination thereof; a sponge; an organism, e.g., a porous material derived from a bone of an organism; and a combination thereof, but the present disclosure is not limited thereto.

The non-conductive glass may include one or more selected from the group consisting of glass wool, glass frit, porous glass, and a combination thereof, but the present disclosure is not limited thereto.

The porous base layer may have a pore size of about 0.1 μm to about 500 μm, in particular, about 5 μm to about 300 μm, and in more particular about 10 μm to about 200 μm.

When the pore size of the porous support satisfies the above range, the fluid and the ions may be effectively moved, thereby improving stability, lifespan characteristics, and efficiency of the pump 100.

The electrochemical reaction material may include a material that may generate a pair of reactions in which an oxidizing electrode and a reducing electrode exchange positive ions, e.g., hydrogen ions, during electrode reactions of the first electrode body 140 and the second electrode body 150, and at the same time, may constitute a reversible electrochemical reaction.

The electrochemical reaction material may include one or more selected from the group consisting of, for example, silver/silver oxide, silver/silver chloride, MnO (OH), polyaniline, polypyrrole, polythiophene, polythionine, quinone-based polymer, and a combination thereof.

The first strip 142 may be disposed at an edge of the first porous plate 141, and the second strip 152 may be disposed at an edge of the second porous plate 151. In addition, the first strip 142 may be connected to a first terminal 143 outside the housing 110, and the second strip 152 may be connected to a second terminal 153 outside the housing 110. The first strip 142 and the second strip 152 may include a conductive material, such as silver copper, or the like.

In an embodiment, fluids having the same phase may be disposed in the inner space of the housing 110. For example, a liquid such as water may be disposed inside the housing 110.

In an embodiment, the inner space of the housing 110 may be completely filled with water. Water, which is a liquid, may be filled in both the first space S1 and the second space S2. In particular, the water may also be filled in an inner space defined by the diaphragm member 190.

By placing the housing 110 in a water bath (not shown) in which a fluid is stored, the inner space of the housing 110 may be entirely filled with the fluid. In order to completely fill a fluid in the inner space of the housing 110, the fluid is filled in the water bath, and the housing 110 is inserted into the water bath to allow the fluid to be completely filled in the inner space.

In another embodiment, the fluid provided in the inner space of the housing 110 may include a first fluid and a second fluid having different phases. The first fluid may include a liquid, such as water, and the second fluid may include a gas, such as air.

The first fluid that exists in the inner space does not entirely fill the inner space. That is, a volume of the inner space is greater than a volume of the first fluid that exists in the inner space. The second fluid exists in a portion in which water does not exist in the inner space.

The first bonding member 160 is disposed to cover a side surface of the membrane assembly MA. The first bonding member 160 may be injected into a gap between the first electrode body 140 and the second electrode body 150 to seal the side surface of the membrane assembly MA. Specifically, the first bonding member 160 may be injected between the first strip 142 and the second strip 152 and may cover a side surface of the membrane 130. By covering the side surface of the membrane 130, the first bonding member 160 may prevent a fluid from leaking through the side surface of the membrane 130.

The first bonding member 160 may be formed of various adhesive materials. For example, the first bonding member 160 may be formed of a silicone or resin-based material. In an example, the first bonding member 160 may be bonded to the side surface of the membrane assembly MA using a silicone thermosetting adhesive.

The membrane assembly MA is manufactured as a unit in which the membrane 130, the first electrode body 140, the second electrode body 150, and the first bonding member 160 are coupled, which allows for space utilization and ease of mounting. In addition, the side surface of the membrane assembly MA is covered by the first bonding member 160 to prevent the fluid from leaking therethrough.

Figure 12:
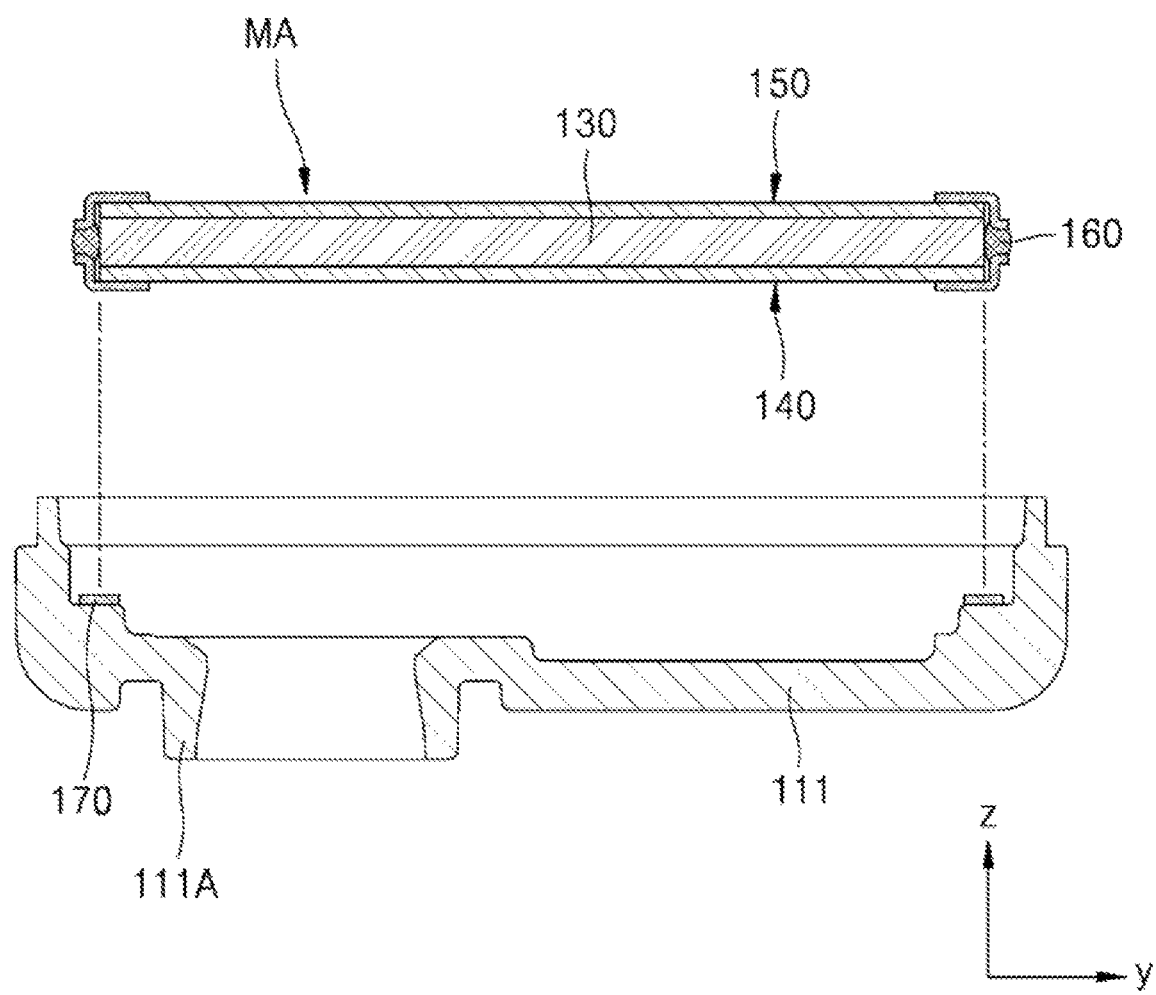
FIGS. 12 and 13 are views illustrating a method of installing the membrane assembly of FIG. 10.
Figure 13:
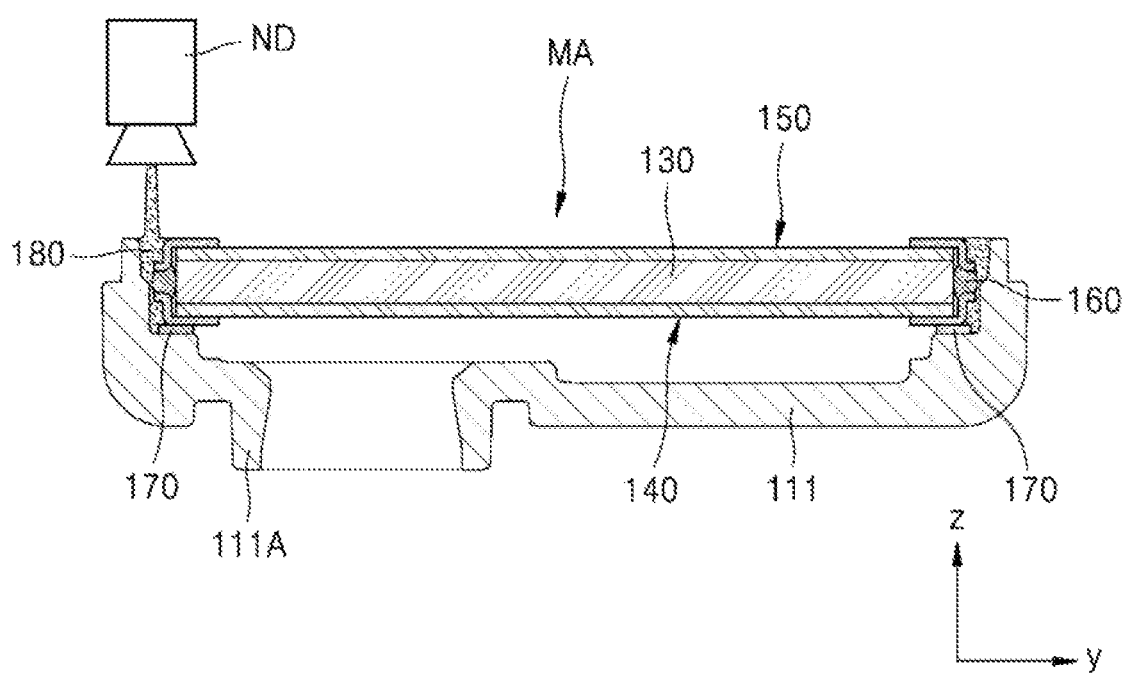

FIGS. 12 and 13 are views illustrating a method of installing the membrane assembly of FIG. 10.

Referring to FIGS. 4, 12, and 13, the membrane assembly MA is fixed to the inner space of the housing 110 by the second bonding member 170 and the third bonding member 180, and may prevent a fluid from leaking to an edge of the membrane assembly MA.

The fluid moves from the first space S1 to the second space S2 or in the reverse direction along a thickness direction of the membrane 130 so as to pass through the membrane 130, and at this time, the first and third bonding members may close a gap between the inner surface of the housing 110 and the membrane assembly MA to prevent the fluid from moving through the gap.

The second bonding member 170 is disposed between one of the first electrode body 140 and the second electrode body 150 and the inner surface of the housing 110 to fix one surface of the membrane assembly MA.

The second bonding member 170 may be formed of a variety of materials that fix both components. The second bonding member 170 may be formed of a silicone or resin-based material. In addition, the second bonding member 170 may be disposed by being applied in a gel form, or may be disposed by attaching a tape thereto.

In an example, as shown in FIG. 12, the second bonding member 170 may have one surface attached to the first body 111 and the other surface attached to the first strip 142. The second bonding member 170 is disposed on a jaw of the first body 111 so as to correspond to the first strip 142, and then the membrane assembly MA may be aligned and attached to the second bonding member 170.

Thereafter, as shown in FIG. 13, the third bonding member 180 may be injected to an outer side of the membrane assembly MA. The third bonding member 180 is a liquid or gel-type adhesive material, and the third bonding member 180 may be injected into a space between the first body 111 and the membrane assembly MA through an injection device ND.

Since the third bonding member 180 has fluidity, the third bonding member 180 may be injected into the gap between the membrane assembly MA and the housing 110 without gaps. At this time, the second bonding member 170 may prevent the third bonding member 180 from entering the first space S1.

The membrane assembly MA has a plurality of sealing structures, and thus, may be firmly fixed to the inside of the electro-osmotic pump 100 and may prevent the fluid from leaking to the edge of the membrane assembly MA.

Since the side surface of the membrane 130 is sealed by the first bonding member 160, in the membrane assembly MA, the fluid may be prevented from leaking to the edge of the membrane 130.

The membrane assembly MA may be fixed to the housing 110 by the second bonding member 170. In addition, the second bonding member 170 is disposed on an upper or lower surface of the membrane assembly MA and an inner surface of the housing 110 to prevent fluid leakage.

The membrane assembly MA may be fixed to the housing 110 by the third bonding member 180. Since the third bonding member 180 covers the edge of the membrane assembly MA, the third bonding member 180 is disposed to cover the outer side of the first bonding member 160. The third bonding member 180 doubly seals the outer side of the membrane assembly MA to prevent the fluid from leaking through the membrane 130. In addition, the third bonding member 180 may be disposed between the first body 111 and the membrane assembly MA to prevent the fluid from leaking through the gap between the housing 110 and the membrane assembly MA.

Referring to FIG. 4 again, the diaphragm member 190 may be mounted on one side of the housing 110. The diaphragm member 190 is elastically deformable, and an internal volume of the diaphragm member 190 may be changed according to the shape deformation.

The diaphragm member 190 is mounted on the opening 111A of the first body 111, and the inner space is connected to the first space S1. The diaphragm member 190 may be fixed to the first body 111 by a fixing ring 195.

The diaphragm member 190 may be changed in shape according to the movement of the fluid inside the electroosmotic pump 100. When the fluid moves from the first space S1 to the second space S2 through the membrane 130 or moves from the second space S2 to the first space S1 through the membrane 130, a force due to a change in the volume of the fluid may be transmitted to the diaphragm member 190.

The diaphragm member 190 buffers the force caused by the change in the volume of the fluid, allowing the shaft assembly 120 to perform a precise linear reciprocating motion.

When the fluid moves from the first space S1 to the second space S2 due to electrochemical reactions in the membrane assembly MA, the diaphragm member 190 may be concavely changed and may buffer the force caused by the change in the volume of the fluid. In addition, when the fluid moves from the second space S2 to the first space S1, the diaphragm member 190 may be convexly changed and may buffer the force caused by the change in the volume of the fluid.

Figure 14:
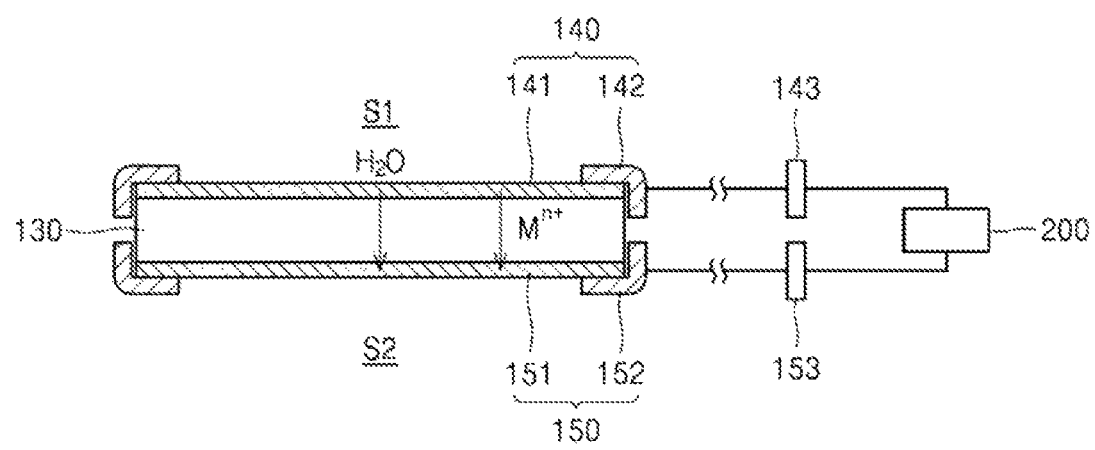
FIGS. 14 and 15 are schematic views illustrating reactions in a first electrode body and a second electrode body with respect to the membrane assembly of FIG. 10.
Figure 15:
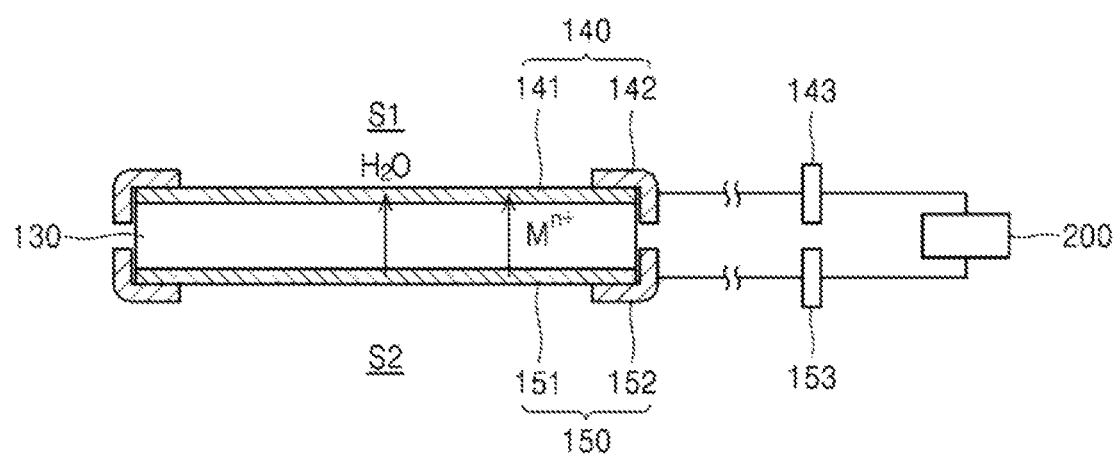

FIGS. 14 and 15 are schematic views illustrating reactions in the first electrode body and the second electrode body with respect to the membrane assembly of FIG. 10.

Referring to FIGS. 14 and 15, the first electrode body 140 and the second electrode body 150 are electrically connected to the power supply 200 via the first terminal 143 and the second terminal 153, respectively. By supplying a voltage supplied by the power supply 200 after alternately changing the polarity of the voltage, a movement direction of the liquid such as water may be changed.

In an embodiment, a case in which silver/silver oxide is used as the electrochemical reaction material and the fluid is a solution including water will be described.

As shown in FIG. 14, when the first electrode body 140 is an oxidizing electrode and the second electrode body 150 is a reducing electrode, a reaction of $Ag(s)+H_2O \rightarrow Ag_2O(s)+2H^++2e^-$ occurs in the first electrode body 140 and a reaction of $Ag_2O(s)+2H^++2e^- \rightarrow Ag(s)+H_2O$ occurs in the second electrode body 150.

Cations ($M^{n+}$, e.g., hydrogen ions) generated according to the oxidation reaction in the first electrode body 140 move toward the second electrode body 150 via the membrane 130 due to a voltage difference, and at this time, water ($H_2O$) moves together with the cations and a predetermined pressure may be generated.

Thereafter, as shown in FIG. 15, when the polarity of the voltage supplied by the power supply 200 is reversed, the electrochemical reaction material that has been consumed when the first electrode body 140 is previously used as the oxidizing electrode is recovered when the first electrode body 140 is used as the reducing electrode. Likewise, the electrochemical reaction material may be also recovered in the reducing electrode, and thus, the first electrode body 140 and the second electrode body 150 may continuously react accordingly to the voltage supply from the power supply 200. Unlike in FIG. 14, when the polarity of the voltage supplied to the first electrode body 140 and the second electrode body 150 is reversed, as shown in FIG. 15, the cations (Mn+, e.g., hydrogen ions) and the water ($H_2O$) move from the second space S2 to the first space S1.

A method of manufacturing the medical liquid injection device 10 may be implemented according to the following operations.

The method of manufacturing the medical liquid injection device may include covering a first bonding member on an outer side of a membrane assembly, aligning the membrane assembly with a first body and attaching the membrane assembly to the first body using a second bonding member, injecting a third bonding member into an edge of the membrane assembly, and assembling a second body to the first body.

In the covering of the first bonding member on the outer side of the membrane assembly, a membrane 130, a first electrode body 140, and a second electrode body 150 are assembled, and a first bonding member 160 is disposed on a side surface of the membrane 130. The first bonding member 160 is disposed in a space between the side surface of the membrane 130 and the first and second electrode bodies 140 and 150, which may prevent a fluid from leaking through the side surface of the membrane 130.

In the aligning of the membrane assembly with the first body and attaching the membrane assembly to the first body using the second bonding member, a second bonding member 170 is attached to a first body 111. The second bonding member 170 may be in the form of a sheet, or may be in the form of a gel. Thereafter, a membrane assembly MA is attached to the second bonding member 170, and the membrane assembly MA is fixed to the first body 111.

In the injecting of the third bonding member to the edge of the membrane assembly, a third bonding member 180 is injected into a space between the membrane assembly MA and the first body 111. The third bonding member 180 has a liquid or gel form, and thus the third bonding member 180 may be deeply injected. At this time, the second bonding member 170 may block the movement of the third bonding member 180, thereby preventing the third bonding member 180 from overflowing into the membrane 130.

In the assembling of the second body to the first body, the first body 111 and the second body 112 may be assembled to complete a housing 110. The first body 111 and the second body 112 are assembled in a forcibly fitting manner and then are coupled to each other by ultrasonic fusion or the like, so that fluid leakage to the outside may be prevented.

It should be noted that the spirit of the present disclosure is not limited to the embodiments described above, and not only the claims to be described later, but also all ranges equivalent to or equivalently changed from the claims fall within the scope of the spirit of the present disclosure.

What is claimed is:

1. A pump comprising:
   a housing having a shaft hole;
   a membrane assembly disposed inside the housing; and
   a shaft assembly mounted on the housing,
   wherein the shaft assembly includes:
   a shaft inserted into the shaft hole; and
   a sealing member disposed on an end portion of the shaft and having a plurality of contact regions on an inner surface of the housing along a longitudinal direction of the shaft,
   wherein the sealing member includes:
   a body into which the shaft is inserted, and having a concave surface disposed forward in an axial direction of the shaft;
   a first protrusion protruding from the body in a radial direction of the shaft;
   a first groove disposed between the body and the first protrusion and having a first depth;
   a second protrusion disposed on a side opposite to the first protrusion; and a second groove disposed between the body and the second protrusion and having a second depth to be different from the first depth; and wherein the shaft includes:

a first supporter disposed inside the sealing member and extending in a radial direction; and a second supporter disposed outside the sealing member and supporting the body of the sealing member.

2. The pump of claim 1, wherein in the sealing member, at least one of the first protrusion and the second protrusion protrudes from an outer circumferential surface of the body.

3. The pump of claim 1, wherein the sealing member includes a sidewall having a concave surface, disposed between the first protrusion and the second protrusion.

* * * * *